US011000585B2

(12) United States Patent
Weaver et al.

(10) Patent No.: US 11,000,585 B2
(45) **Date of Patent: *May 11, 2021**

(54) COMPOSITION COMPRISING ANTIGENS AND A MUCOSAL ADJUVANT AND A METHOD FOR USING

(71) Applicant: Phibro Animal Health Corporation, Teaneck, NH (US)

(72) Inventors: Grant Weaver, Kingsley, IA (US); Jeffrey Alan Kula, Lincoln, NE (US); Boh Chang Lin, Omaha, NE (US); Karen Brown, Parksville, MO (US); Wesley W. Johnson, Platte City, MO (US); Michael Dennis Murphy, Atlantic, IA (US)

(73) Assignee: Phibro Animal Health Corporation, Teaneck, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,877

(22) Filed: Mar. 14, 2019

(65) Prior Publication Data

US 2019/0231864 A1 Aug. 1, 2019

Related U.S. Application Data

(63) Continuation of application No. 15/593,223, filed on May 11, 2017, now Pat. No. 10,279,031, which is a continuation-in-part of application No. PCT/US2016/031902, filed on May 11, 2016.

(60) Provisional application No. 62/334,971, filed on May 11, 2016.

(51) Int. Cl.

| | |
|---|---|
| ***A61K 39/145*** | (2006.01) |
| ***A61K 39/12*** | (2006.01) |
| ***A61K 39/102*** | (2006.01) |
| ***C12N 7/00*** | (2006.01) |
| *A61K 39/00* | (2006.01) |

(52) U.S. Cl.

CPC .......... *A61K 39/145* (2013.01); *A61K 39/102* (2013.01); *A61K 39/12* (2013.01); *C12N 7/00* (2013.01); *A61K 2039/543* (2013.01); *A61K 2039/552* (2013.01); *A61K 2039/55505* (2013.01); *A61K 2039/55511* (2013.01); *A61K 2039/55555* (2013.01); *A61K 2039/55566* (2013.01); *C12N 2760/16134* (2013.01)

(58) Field of Classification Search

None

See application file for complete search history.

(56) References Cited

U.S. PATENT DOCUMENTS

| | | | | |
|---|---|---|---|---|
| 4,235,601 A | | 11/1980 | Deutsch | |
| 4,562,147 A | | 12/1985 | Joo | |
| 4,944,942 A | * | 7/1990 | Brown | A61K 9/0043 424/244.1 |
| 5,591,645 A | | 1/1997 | Rosenstein | |
| 5,690,940 A | | 11/1997 | Joo | |
| 5,888,513 A | | 3/1999 | Plana Duran et al. | |
| 6,251,397 B1 | | 6/2001 | Paul et al. | |
| 6,380,376 B1 | | 4/2002 | Paul et al. | |
| 6,592,873 B1 | | 7/2003 | Paul et al. | |
| 6,673,342 B1 | | 1/2004 | Capra et al. | |
| 6,682,745 B1 | | 1/2004 | Jacobs et al. | |
| 6,773,908 B1 | | 10/2004 | Paul et al. | |
| 7,241,582 B2 | | 7/2007 | Joo et al. | |
| 8,968,744 B2 | | 3/2015 | Mombarg | |
| 10,279,031 B2 | * | 5/2019 | Weaver | A61K 39/145 |
| 2003/0064079 A1 | | 4/2003 | Goudie et al. | |
| 2003/0186225 A1 | | 10/2003 | Paul et al. | |
| 2005/0220814 A1 | | 10/2005 | Dominowski et al. | |
| 2006/0127885 A1 | | 6/2006 | Kang et al. | |
| 2008/0019912 A1 | | 1/2008 | Harris et al. | |

(Continued)

FOREIGN PATENT DOCUMENTS

| | | | |
|---|---|---|---|
| CN | 102949714 A | * | 3/2013 |
| CN | 104 511 015 | | 4/2015 |

(Continued)

OTHER PUBLICATIONS

Shaikh et al. (Journal of Pharmacy and BioAllied Sciences. Jan.-Mar. 2011; 3 (1): 89-100).*

Hou et al. Machine Translation of CN104208667 published Dec. 2014.*

Espacenet translation of CN 102949714A Mar. 3, 2013.*

Polly et al. (The Journal of Infectious Diseases. Mar. 1975; 131 (3): 217-224).*

Cancel-Tirado et al., "Monoclonal antibody analysis of porcine reproductive and respiratory syndrome virus epitopes associated with antibody-dependent enhancement and neutralization of virus infection," *Veterinary Immunology and Immunopathology* 102:249-262, 2004.

(Continued)

*Primary Examiner* — Shanon A. Foley

(74) *Attorney, Agent, or Firm* — Klarquist Sparkman, LLP

(57) ABSTRACT

The majority of the mortality observed in young pigs occurs between three and five weeks post-weaning for *S. suis* infections and between four and six weeks post-weaning for *H. parasuis* and *Actinobacillus suis* infections. Clinical disease control associated with *S. suis, A. suis* and *H. parasuis* has been attempted using antibiotic treatment, by controlled exposure with live organisms, and by vaccination, using either inactivated commercial or autogenous bacterins administered parenterally. A similar lack of protection in very young pigs is observed with various viruses including swine influenza virus, porcine reproductive and respiratory syndrome virus, porcine epidemic diarrhea virus and rotavirus. Disclosed herein is an immunogenic composition comprising inactivated antigens and a mucosal adjuvant. The composition may be administered to subjects, such as animals, particularly piglets from pre-weaning through the nursery phase, such as from birth or from three to five days of age, to protect from these diseases.

25 Claims, 5 Drawing Sheets

Specification includes a Sequence Listing.

(56) References Cited

U.S. PATENT DOCUMENTS

| | | | | |
|---|---|---|---|---|
| 2008/0026988 | A1* | 1/2008 | Baker, Jr. | A61K 39/12 424/188.1 |
| 2009/0117512 | A1 | 5/2009 | Chu et al. | |
| 2011/0038900 | A1 | 2/2011 | Chaprapani et al. | |
| 2011/0123570 | A1 | 5/2011 | Kroll et al. | |
| 2011/0150770 | A1* | 6/2011 | Bautista | A61P 31/04 424/9.2 |
| 2013/0302370 | A1* | 11/2013 | Fachinger | A61P 31/06 424/204.1 |
| 2014/0004144 | A1 | 1/2014 | Bey et al. | |
| 2014/0255442 | A1 | 9/2014 | Burgard et al. | |
| 2015/0266933 | A1* | 9/2015 | Baker, Jr. | C07K 14/32 424/246.1 |
| 2017/0179594 | A1 | 6/2017 | Liao et al. | |
| 2017/0326226 | A1 | 11/2017 | Weaver et al. | |
| 2019/0231864 | A1* | 8/2019 | Weaver | A61K 39/102 |

FOREIGN PATENT DOCUMENTS

| | | |
|---|---|---|
| CN | 110 075 289 | 8/2019 |
| EP | 1 001 025 | 5/2000 |
| WO | WO 1996/006619 | 3/1996 |
| WO | WO 1999/039582 | 8/1999 |
| WO | WO 2000/053787 | 9/2000 |
| WO | WO 2002/095040 | 11/2002 |
| WO | WO 2014/004361 | 1/2014 |

OTHER PUBLICATIONS

Charerntantanakul et al., "Immune responses and protection by vaccine and various vaccine adjuvant candidates to virulent porcine reproductive and respiratory syndrome virus," *Veterinary Immunology and Immunopathology* 109(1-2):99-115, Feb. 2006.

Cho et al., "An ELISA of Porcine Reproductive and Respiratory Syndrome: Production of Antigen of High Quality," *Canadian Journal of Veterinary Research* 60(2):89-93, May 1996.

Cho et al., "Performance of ELISA Antigens Prepared from 8 Isolates of Porcine Reproductive and Respiratory Syndrome Virus with Homologous and Heterologous Antisera," *Canadian Journal of Veterinary Research* 61(4):299-304, Oct. 1997.

Delputte et al., "Involvement of the Matrix Protein in Attachment of Porcine Reproductive and Respiratory Syndrome Virus to a Heparin-like Receptor on Porcine Alveolar Macrophages," *Journal of Virology* 76(9):4312-4320, May 2002.

Denac et al., "An indirect ELISA for the detection of antibodies against porcine reproductive and respiratory syndrome virus using recombinant nucleocapsid protein as antigen," *Journal of Virological Methods* 65(2):169-181, 1997.

Faaberg et al., "Neutralizing antibody responses of pigs infected with natural GP5 N-glycan mutants of porcine reproductive and respiratory syndrome virus," *Viral Immunology* 19(2):294-304, Summer 2006.

Fernandez et al., "Porcine reproductive and respiratory syndrome virus (PRRSV) envelope GP5 protein fails to protect pigs against PRRSV," *4th International Symposium on Emerging and Re-Emerging Pig Diseases*, Rome, Italy, Jun. 29-Jul. 2, 2003.

Gonin et al., "Seroneutralization of porcine reproductive and respiratory syndrome virus correlates with antibody response to the GP5 major envelope glycoprotein," *Journal of Veterinary Diagnostic Investigation* 11:20-26, 1999.

Meulenberg et al., "Localization and Fine Mapping of Antigenic Sites on the Nucleocapsid Protein N of Porcine Reproductive and Respiratory Syndrome Virus with Monoclonal Antibodies," *Virology* 252:106-114, 1998.

Nelson et al., "Serum immune responses to the proteins of porcine reproductive and respiratory syndrome (PRRS) virus," *Journal of Veterinary Diagnostic Investigation* 6:410-415, 1994.

Nielsen et al., "Reversion of a live porcine reproductive and respiratory syndrome virus vaccine investigated by parallel mutations," *Journal of General Virology* 82:1263-1272, 2001.

Ostrowski et al., "Identification of Neutralizing and Nonneutralizing Epitopes in the Porcine Reproductive and Respiratory Syndrome Virus GP5 Ectodomain," *Journal of Virology* 76(9):4241-4250, May 2002.

Pirzadeh et al., "Immune response in pigs vaccinated with plasmid DNA encoding ORF5 of porcine reproductive and respiratory syndrome virus," *Journal of General Virology* 79:989-999, 1998.

Plana-Duran et al., "New strategies on vaccinology: Use of the transmissible gastroenteritis virus as a vector for swine disease," *4th International Symposium on Emerging and Re-Emerging Pig Diseases*, Rome, Italy, Jun. 29-Jul. 2, 2003.

Rodriguez et al., "Identification of an immunodominant epitope in the C terminus of glycoprotein 5 of porcine reproductive and respiratory syndrome virus," *Journal of General Virology* 82:995-999, 2001.

Rogan et al., "Novel vaccines from biotechnology," *Revue Scientifique et Technique* (*International Office of Epizootics*) 24(1):159-174, 2005.

Wagner et al., "Protection against heterologous PRRSV challenge in pregnant sows immunized with multivalent PRRS vaccine," *International PRRS Symposium*, St. Louis, MO, Dec. 2-3, 2005.

Yeager, "The effect of vaccination with combinations of commercial PPRSV vaccines on the development of serum neutralizing antibodies to 6 antigenically different strains of PPRSV," *Research Report Swine Health* NPB #99-035, National Pork Board, Aug. 1, 2000.

Yoon et al., "Isolation of a cytopathic virus from weak pigs on farms with a history of swine infertility and respiratory syndrome," *Journal of Veterinary Diagnostic Investigation* 4(2):139-143, 1992.

Yoon et al., "A modified serum neutralization test for the detection of antibody to porcine reproductive and respiratory syndrome virus in swine sera," *Journal of Veterinary Diagnostic Investigation* 6(3):289-292, Jul. 1994.

Chaturvedi et al., "A review on mucoadhesive polymer used in nasal drug delivery system," *Journal of Advanced Pharmaceutical Technology & Research* 2(4):215-222, Oct. 1, 2011.

Mangal et al., "Evaluation of mucoadhesive carrier adjuvant: Toward an oral anthrax vaccine," *Artificial Cells, Nanomedicine, and Biotechnology* 42:47-57, 2014.

Wang et al., "Intranasal and oral vaccination with protein-based antigens: advantages, challenges and formulation strategies," *Protein Cell* 6(7):480-503, 2015.

Aoshi, "Modes of Action for Mucosal Vaccine Adjuvants," *Viral Immunology* 30(6):463-470, 2017.

Bijlenga et al., "Development and use of the H strain of avian infectious bronchitis virus from the Netherlands as a vaccine: a review," *Avian Pathology* 33(6):550-557, Dec. 2004.

Dandapat et al., "Induction of Mucosal Immunity in Poultry After Oral Immunization with a Single Dose of Microencapsulated EDS-76 Virus," *Indian Journal of Comparative Microbiology, Immunology and Infectious Diseases* 24(2):181-185, 2003.

Davelaar et al., "Vaccination of 1-day-old broilers against infectious bronchitis by eye drop application or coarse droplet spray and the effect of revaccination by spray," *Avian Pathology* 9(4):499-510, 1980.

Guo et al., "Evaluation of protective efficacy of a novel inactivated *Salmonella pullorum* ghost vaccine against virulent challenge in chickens," *Veterinary Immunology and Immunopathology* 173 :27-33, 2016.

Ismail et al., "IMS 1313-nanoparticle Mucosal Vaccine Enhances Immunity Against Avian Influenza and Newcastle Disease Viruses," *International Journal of Poultry Science* 17(4):167-174, 2018.

MONTANIDE™ IMS, pp. 1-4, 2020 ( https://www.seppic.com/en/montanide-ims).

Nochi et al., "The Well-Developed Mucosal Immune Systems of Birds and Mammals Allow for Similar Approaches of Mucosal Vaccination in Both Types of Animals," *Frontiers in Nutrition* vol. 6, Article 60, pp. 1-8, Jul. 2018.

Winterfield et al., "Immunity to Infectious Bronchitis Virus from Spray Vaccination with Derivatives of a Holland Strain," *Avian Diseases* 20(1):42-48, 1976.

(56) References Cited

OTHER PUBLICATIONS

Winterfield et al., “Vaccination and Revaccination with a Holland (H) Strain of Infectious Bronchitis Virus,” *Avian Diseases* 20(2):369-374, 1976.

* cited by examiner

COMPOSITION COMPRISING ANTIGENS AND A MUCOSAL ADJUVANT AND A METHOD FOR USING

CROSS REFERENCE TO RELATED APPLICATIONS

This application is a continuation of U.S. patent application Ser. No. 15/593,223, filed on May 11, 2017, which is a continuation-in-part application of International Application No. PCT/US2016/031902, filed on May 11, 2016, and also claims priority to U.S. provisional patent application No. 62/334,971, filed on May 11, 2016. Both applications are incorporated herein by reference in their entireties.

FIELD

This disclosure relates to a composition comprising antigens and a mucoadhesive adjuvant, and methods of making and using the composition.

BACKGROUND

Major economic losses in commercial swine nursery facilities are caused by diseases spread via the respiratory route. These include *Streptococcus suis*-related infections, *Actinobacillus suis*-related infections, *Haemophilus parasuis* related to Glässer's Disease, *Mycoplasma* infections caused by *Mycoplasma hyorhinis* or *Mycoplasma hyosynoviae, Actinobacillus pleuropneumoniae*-related infections, *Pasteurella*-related infections cause by *Pasteurella multocida*, infections caused by *Bordetella bronchiseptica, Erysipelothrix rhusiopathiae, Salmonella* spp. including *Salmonella cholerasuis* and *Salmonella typhimurium, Escherichia coli*, swine influenza viruses, porcine reproductive and respiratory syndrome viruses (PRRSv) and disease caused by porcine epidemic diarrhea virus (PEDV). The majority of the mortality observed in these young pigs occurs between three and five weeks post-weaning for *S. suis* infections and between four and six weeks post-weaning for *H. parasuis* infections.

*S. suis* produces signs and/or symptoms including meningitis, polyserositis, arthritis, myocarditis, pericarditis and abortion. *H. parasuis* often produces an acute septicemia that leads to death. Additionally, the latter is an important component in the Porcine Respiratory Disease Complex. *A. suis* and the *Mycoplasma* species are common respiratory diseases of pigs that are transmitted by nose-to-nose contact. *M. hyopneumoniae* and *M. hyorhinis* both produce significant respiratory disease, whereas *M. hyosynoviae* more commonly causes arthritis resulting in lameness. *B. bronchiseptica* also results in a respiratory disease that is called atrophic rhinitis. *P. multocida* is another organism associated with atrophic rhinitis and that is spread via mucous membranes. Swine influenza virus and PRRS also produce significant respiratory diseases in pigs. PRRS is also associated with a reproductive syndrome causing abortion. On the other hand, the *Salmonella* species, *E. coli* and PEDV cause intestinal diseases that result in diarrhea that can kill neonates and young very quickly.

Attempts have been made to control clinical disease associated with all of the bacterial species, including *S. suis, H. parasuis* and *A. suis*, by antibiotic treatment, by controlled exposure to live organisms, and by vaccination using inactivated, parenterally-injected bacterial vaccines (bacterins). A currently accepted strategy for protecting weaned pigs entering this stage of production involves vaccination using appropriate bacterins at the standard time of piglet processing followed by revaccination at weaning. Such vaccinations utilize inactivated antigens that are administered either intramuscularly or subcutaneously (parenteral).

In commercial settings, sows and gilts are often already exposed to the diseases for which their offspring, especially neonatal offspring, will be susceptible. When sows or gilts are seropositive because of previous exposure or vaccination, they transfer lactogenic antibodies to their neonatal offspring, which may protect the neonates for a period of time. Unfortunately, such maternal antibodies often interfere with the neonate being able to produce their own antibodies if they are vaccinated at too young an age with a parenteral vaccine. Parenteral vaccination mainly stimulates the development of IgG and IgM antibodies.

In 1989, pork producers in the United States developed the Pork Quality Assurance program, a producer education and certification program to reduce the risk of animal health product residues in pork. In 2007, this program was enhanced and became known as Pork Quality Assurance Plus (PQA)Plus®. One of the aspects of this program is to reduce the use of parenteral injections, especially in young pigs, helping to ensure the safety of food products.

SUMMARY

The present disclosure describes embodiments of a composition comprising inactivated bacterial antigens and a mucosal adjuvant, such as a mucoadhesive adjuvant. The composition can be administered mucosally, such as intranasally, to animals, such as pigs, particularly neonates, to immunize them again against typical neonatal and nursery diseases. Mucosal, such as intranasal, administration of the composition may stimulate the production of IgA, a mucosal antibody which may overcome maternal antibody interference. In a commercial setting, the intranasal administration technique has several other distinct advantages when compared with traditional parenteral vaccination. Such advantages include ease of administration at processing, lessened risk of tissue loss due to needle use, and reduction of workload. Furthermore, the mucosal route may be less susceptible to maternal immunity interference.

Mucosal vaccination, such as intranasal vaccination, is used for non-inactivated antigens, such as administering a live virulent virus or bacteria, a live attenuated virus or bacteria, a modified live virus or bacteria, a live vectored viral or bacterial antigen, or a combination thereof. However, those viruses or bacteria (herein defined as live antigens) protect by causing either a low-level of infection or a replication in the animal, which stimulates an immune response. No inactivated or killed antigens have been delivered mucosally, including intranasally, to pigs and demonstrated to either stimulate an IgA response or produce a protective response. Such an intranasal method of immunizing pigs would also meet the requirements of the PQA.

Disclosed herein are embodiments of a composition comprising one or more inactivated antigens obtained from one or more bacterial strains and/or one or more viral, strains, subunits, recombinant proteins and/or peptides from bacterial or viral antigens, and a mucosal, such as a mucoadhesive, adjuvant. Inactivated antigens that may be included in such a composition are antigens from bacterial strains such as *S. suis, H. parasuis, A. suis, M. hyorhinis, M. hyosynoviae, P. multocida, B. bronchiseptica, E. rhusiopathiae, S. cholerasuis, S. typhimurium, E. coli, C. perfringens, C. difficile*, or combinations thereof; virus antigens that may be included in such compositions include but are not limited to swine influenza viruses, such as H1N1, H3N2, H1N2, H2N3, or a combination thereof; porcine rotavirus groups A, B and C; PRRS; and/or PEDV. In some embodiments, the composition comprises one or more inactivated antigens obtained from one or more bacterial strains, such as *S. suis*, *H. parasuis*, and/or *A. suis*, and a mucosal, such as a mucoadhesive, adjuvant. Other inactivated antigens that may be included in such a composition are *M. hyorhinis, M. hyosynoviae, P. multocida, B. bronchiseptica, E. rhusiopathiae, S. cholerasuis, S. typhimurium, E. coli, C. perfringens, C. difficile*, swine influenza viruses, porcine rotavirus groups A, B and C, PRRS, and/or PEDV.

Other disclosed embodiments include certain inactivated viral antigens such as inactivated swine influenza (SIV or IAV-S), inactivated Porcine Respiratory and Reproductive Syndrome Virus (PRRSv), inactivated Porcine Epidemic Diarrhea Virus (PEDV) and other viruses that may be spread by inhalation of the virus.

In some embodiments, the composition does not comprise a nanoparticle. In other embodiments, the composition does not comprise a nanoparticle that comprises one or more biodegradable polymers.

Also disclosed are embodiments of a method of administering the composition to a subject, particularly an animal, such as a pig. The composition may be formulated for mucosal administration to pigs, such as intranasal administration. Administration of the composition may induce an immune response in the subject. The immune response may comprise an increased IgA response compared to an animal not administered the composition. Mucosal administration may reduce the severity and incidence of disease when the animal is later challenged by exposure to live organisms. Adjuvants with mucoadhesive characteristics include, but are not limited to, polymers, such as those comprising Carbopols or acrylic acids (such as polyacrylic acids), such as Carbigen™ adjuvant; oil-in-water based adjuvants, such as Emulsigen® adjuvant; nanoparticles; or combinations thereof. The adjuvants may include immunostimulators, such as dimethyldioctadecyl ammonium bromide (DDA) or chloride (DDAC), pluronics, aluminum hydroxide, aluminum phosphate, and others known to persons of ordinary skill in the art.

Accordingly, disclosed embodiments concern an immunogenic composition comprising one or more strains of inactivated *S. suis*, one or more strains of inactivated *H. parasuis* and/or one or more strains of *A. suis*. The disease-producing organisms including one or more isolates or strains of *H. parasuis, A. suis* and/or *S. suis* may originally have been isolated from a diseased animal. The bacteria can be grown in culture media to appropriate titers, such as at least $10^5$ colony forming units/mL (CFU/mL), and then inactivated prior to incorporation into a vaccine for administering mucosally.

Additionally, certain embodiments of the composition stimulate an IgA response when administered intranasally to neonatal pigs. Without being bound to a particular theory, the IgA response may be able to overcome inhibition by maternal antibodies that are delivered to the neonate by the sow or gilt.

Certain disclosed embodiments include multivalent immunogenic compositions comprising a combination of antigens from at least two of *S. suis, H. parasuis*, and *A. suis* that have been inactivated with an acceptable inactivating agent and a mucosal, such as a mucoadhesive, adjuvant. The multivalent immunogenic composition may comprise antigens from all three organisms. The combination may be then administered to pigs via a mucosal route. One or more administrations may be performed to produce protection from disease. Acceptable inactivating agents for use with these antigens include, but are not limited to, formaldehyde, formalin, binary ethyleneimine, thimerosal, beta propiolactone, detergents such as NP40 and Triton X 100, and combinations thereof. Antigens may include whole culture bacteria, subunits that have been extracted or separated from the culture, antigens obtained from recombinant organisms other than *S. suis, H. parasuis* or *A. suis* but which protect against *S. suis, H. parasuis* or *A. suis* infection or challenge, or a combination thereof. Infection or challenge means that the animal suffers one or more clinical signs of the *S. suis, A. suis* or *H. parasuis* diseases when they have been exposed to these live organisms.

In specific embodiments, one or more of the *S. suis, A. suis* or *H. parasuis* antigens are present in the composition in an amount of from about $10^2$ to about $10^{10}$ CFU/mL. The composition may further include a suitable pharmaceutical carrier, such as a diluent, adjuvant, antimicrobial agent, preservative, inactivating agent, or combination thereof. Antimicrobial agents can include, but are not limited to, antibiotics such as gentamicin, penicillin, neomycin, polymyxin B and mycostatin.

Also disclosed herein are embodiments of a method for reducing the incidence or lessening the severity of clinical signs associated with or caused by bacterial infections, such as infection by *S. suis, A. suis* and/or *H. parasuis*. In some embodiments, the method comprises reducing the incidence or lessening the severity of clinical signs associated with or caused by additional bacterial infections, such as infection by *M. hyorhinis, M. hyosynoviae, P. multocida, B. bronchiseptica, E. rhusiopathiae, S. cholerasuis, S. typhimurium, E. coli*, swine influenza viruses, PRRS, or PEDV comprising administering the composition to a subject, such as a pig, via a mucosal, such as intranasal, route. And embodiments of a method of vaccinating swine against diseases of *S. suis, H. parasuis, A. suis, M. hyorhinis, M. hyosynoviae, P. multocida, B. bronchiseptica, E. rhusiopathiae, S. cholerasuis, S. typhimurium, E. coli*, swine influenza viruses, PRRS, PEDV, or a combination thereof, by administering inactivated antigens of *S. suis, H. parasuis, A. suis, M. hyorhinis, M. hyosynoviae, P. multocida, B. bronchiseptica, E. rhusiopathiae, S. cholerasuis, S. typhimurium, E. coli*, swine influenza viruses, PRRS, PEDV or a combination thereof, to a subject, such as a pig, by an intranasal route, are also disclosed.

The foregoing and other objects, features, and advantages of the invention will become more apparent from the following detailed description, which proceeds with reference to the accompanying figures.

SEQUENCE LISTING

Figure 1:
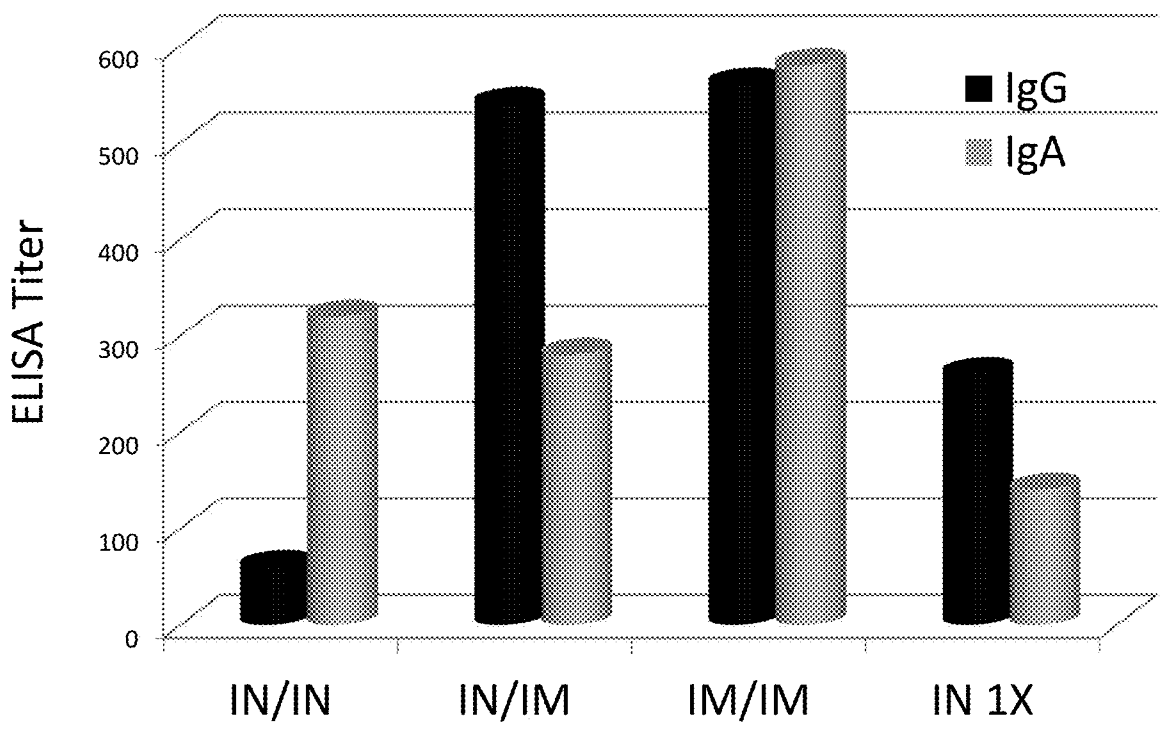
FIG. 1 is a graph of ELISA titer versus administration protocol, illustrating the measured IgA and IgG serum levels resulting from the various administration protocols, establishing that intranasal administration resulted in the production of IgA and IgG antibodies in the pigs.

The nucleic and amino acid sequences listed in the accompanying sequence listing are shown using standard letter abbreviations for nucleotide bases, and three letter code for amino acids, as defined in 37 C.F.R. § 1.822. Only one strand of each nucleic acid sequence is shown, but the complementary strand is understood as included by any reference to the displayed strand. The Sequence Listing is submitted as an ASCII text file, created on May 11, 2017, 20 MB, which is incorporated by reference herein.

DETAILED DESCRIPTION

I. Definitions

The following explanations of terms and methods are provided to better describe the present disclosure and to guide those of ordinary skill in the art in the practice of the present disclosure. The singular forms “a,” “an,” and “the” refer to one or more than one, unless the context clearly dictates otherwise. The term “or” refers to a single element of stated alternative elements or a combination of two or more elements, unless the context clearly indicates otherwise. As used herein, “comprises” means “includes.” Thus, “comprising A or B,” means “including A, B, or A and B,” without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term “about.” Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word “about” is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

The term “adjuvant” as used herein means any component added to a vaccine that enhances the immune response and includes any adjuvant suitable for administration to an animal subject. In some embodiments, the adjuvant is, or comprises, a carbomer-based or carbopol-based polymer, such as Carbigen™ adjuvant (MVP adjuvants, a Division of Phibro Animal Health, Omaha, Nebr., USA), HRA-3, and HRA-5; an aluminum salt, such as aluminum hydroxide or aluminum phosphate; a saponin such as Quil A® adjuvant or Stimulon™ adjuvant QS-21 (Antigenics, Framingham, Mass.); an oil-in-water adjuvant such as an Emulsigen® adjuvant (MVP adjuvants, a Division of Phibro Animal Health Corporation, Omaha, Nebr., USA) containing a non-metabolizable oil, paraffin oil, mineral and/or plant/vegetable and/or animal oils; a surfactant; a lipid; nanoparticles including but not limited to oil-in-water based nanoparticles; cholesterol; water-in-oil emulsions; water-in-oil-in water emulsions; dimethyldioctadecyl ammonium bromide; dimethyldioctadecyl ammonium chloride; or combinations thereof. In adjuvants comprising emulsions, the emulsion can be based in particular on light liquid paraffin oil, isoprenoid oil such as squalane or squalene, oil resulting from the oligomerization of alkenes, in particular of isobutene or decene, esters of acids or of alcohols containing a linear alkyl group, more particularly plant oils, ethyl oleate, propylene glycol di-(caprylate/caprate), glyceryl tri-(caprylate/caprate) or propylene glycol dioleate, esters of branched fatty acids or alcohols, in particular isostearic acid esters. The oil may be used in combination with emulsifiers to form the emulsion. The emulsifiers are preferably nonionic surfactants, in particular esters of sorbitan, of mannide, of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products. In a preferred embodiment of the composition, the adjuvant is at a concentration of from 0.01% to 70%, such as from 1% to 50%, 1% to 30%, 5% to 20%, 7% to 20%, or 10% to 20% by volume of the final product.

Bacterial antigens suitable for use in the present technology include proteins, polysaccharides, lipopolysaccharides, and/or outer membrane vesicles which may be purified, isolated or derived from a bacterium. Bacterial antigens also may include bacterial lysates and inactivated bacteria formulations. In some embodiments, bacteria antigens may be produced by recombinant expression. Typically, bacterial antigens include epitopes which are exposed on the surface of the bacteria during at least one stage of a life cycle. Bacterial antigens may be conserved across multiple serotypes. Bacterial antigens include antigens derived from one or more of the bacteria disclosed herein.

Viral antigens suitable for use in the present technology include inactivated (or killed) virus and/or viral proteins which may be isolated, purified or derived from a virus. Viral antigens can be derived from viruses propagated on a substrate, such as a cell culture or other substrate, or they may be derived or expressed recombinantly. Typically, viral antigens include epitopes which are exposed on the surface of the virus during at least one stage of a life cycle. Viral antigens may be conserved across multiple serotypes or isolates. Viral antigens include antigens derived from one or more of the viruses disclosed herein.

The terms “mucoadhesive,” “mucosal adjuvant,” or “mucosally-adjuvanted” refer to an adjuvant that has the capability to adhere to mucosal membranes and stimulate an immune response. Mucous membranes include the nasopharyngeal, oral, optic (eye), vaginal or anal membranes. The immune response that is stimulated may include IgA, IgG, IgM, or a combination thereof, which are found in the serum and in mucosal washings. Compositions comprising such adjuvants are applied to the mucosal membranes of animals. Specific adjuvants with mucoadhesive characteristics include, but are not limited to, adjuvants comprising polymers, such as those comprising polyacrylic acids such as Carbopols or Carbomers (e.g. Carbigen™ adjuvant, HRA-3, HRA-5, Carbigen-M, Carbigen-P, or combinations thereof); or oil-in-water based adjuvants, such as Emulsigen® adjuvant, Emulsigen®-D adjuvant, Emulsigen®-DL90 adjuvant, Emulsigen®-BCL adjuvant, Emulsigen®-P adjuvant, Emulsigen®-M adjuvant, and combinations thereof. Additionally, adjuvants containing nanoparticles can be used for intranasal administration. A person of ordinary skill in the art understands that a mucoadhesive adjuvant could contain any combination of the above adjuvants as well. Acceptable mucoadhesive adjuvants also include any adjuvant that when administered mucosally, such as intranasally, stimulates an IgA response in pigs and/or protects pigs from challenge with a live organism.

Formulations for mucosal administration, including intranasal formulations, may comprise vehicles that neither cause irritation to the nasal mucosa nor significantly disturb ciliary function. Diluents such as water, aqueous saline, phosphate buffered saline (PBS), culture medias, or other known substances can be used in combination with other components of disclosed compositions. The nasal formulations may also contain preservatives such as, but not limited to, gentamicin, formaldehyde, formalin, thimerosal, binaryethyleneimine, and/or beta propiolactone, and/or may contain neutralizing agents such as sodium thiosulfate and/or sodium bisulfite. A surfactant may be present to enhance absorption of the subject proteins by the nasal mucosa. Acceptable surfactants include but are not limited to tweens, spans and detergents such as NP40 and Triton X 100.

Acceptable inactivating agents for inactivating bacterial antigens, such as *S. suis, A. suis* and/or *H. parasuis* antigens, or viral antigens such as SIV (IAV-S), PRRS and PEDV, include, but are not limited to, formaldehyde, formalin, binary ethyleneimine, thimerosal, beta-propiolactone, and combinations thereof.

Infection or challenge means that the subject has been exposed to live organisms that may produce disease causing the subject to suffer one or more clinical signs of the diseases when they have been exposed to these live organisms.

The term "effective amount" or "therapeutically effective amount" refers to the amount of an active agent (such as one or more embodiments provided herein alone, in combination, or potentially in combination with other therapeutic agent(s)) sufficient to induce a desired biological result. That result may be amelioration or alleviation of the signs, symptoms, or causes of a disease, or any other desired alteration of a biological system. The term "effective amount" or "therapeutically effective amount" is used herein to denote any amount of a therapeutic and/or preventative that causes an improvement in a disease condition, or prevention of disease symptoms. The amount can vary with the condition being treated, the stage of advancement of the condition, and the type and concentration of formulation applied. Appropriate amounts in any given instance will be readily apparent to those of ordinary skill in the art or capable of determination by routine experimentation such as vaccination and observation of an antibody response or vaccination followed by a challenge wherein the vaccinated animals perform better than non-vaccinated animals that are challenged similarly.

II. Composition

Disclosed herein are embodiments of a composition comprising one or more inactivated antigens and an adjuvant, such as a mucoadhesive adjuvant. The antigens may be any suitable antigen, but certain embodiments particularly may be obtained from one or more bacterial strains, particularly strains of *S. suis, A. suis* and/or *H. parasuis* and/or one or more viruses such as SIV (IAV-S), PRRSv and PEDV. The composition may be formulated for mucosal administration to a subject to stimulate an immune response, the response helping to reduce the severity and incidence of disease when the subject is later challenged by exposure to live organisms. The subject may be a human or an animal. The term "animal" refers to a non-human animal. The animal may be a mammal, such as a swine or pig. The immune response may comprise an IgA immune response.

In some embodiments, the composition comprises inactivated antigens from one or more *S. suis* strains or serovars, such as from 1, 2, 3, 4, 5, 6, 7, 8, 9, 10 or more *S. suis* strains or serovars. In some embodiments, the composition comprises inactivated antigens from one or more *H. parasuis* strains or serovars, such as from 1, 2, 3, 4, 5, 6, 7, 8, 9, 10 or more *H. parasuis* strains or serovars. In some embodiments, the composition comprises inactivated antigens from one or more *A. suis* strains or serovars, such as from 1, 2, 3, 4, 5, 6, 7, 8, 9, 10 or more *A. suis* strains or serovars. The composition may comprise inactivated antigens from one or more *S. suis* strains or serovars and one or more *H. parasuis* strains or serovars; inactivated antigens from one or more *A. suis* strains or serovars and one or more *H. parasuis* strains or serovars; inactivated antigens from one or more *S. suis* strains or serovars and one or more *A. suis* strains or serovars, or inactivated antigens from one or more *S. suis* strains or serovars, one or more *H. parasuis* strains or serovars, and one or more *A. suis* strains or serovars.

In some embodiments, the one or more antigens from *S. suis* comprise one or more antigens from serovars ½, 2, or 3. Additionally, or alternatively, the composition may comprise one or more antigens having at least a 85% sequence identity (i.e., 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to any strain and/or serovar of *S. suis* currently known or later discovered or developed, such as, but not limited to, strains identified by the GenBank Accession numbers AM946016.1, FM252031.1, or NC_012926.1, and/or by SEQ ID NO: 1, SEQ ID NO: 2, or SEQ ID NO: 3, and particularly to serovars ½, 2, or 3. In some embodiments, the one or more antigens from *H. parasuis* comprise one or more antigens from serovars 2 or 7. Additionally, or alternatively, the composition may comprise one or more antigens having at least a 85% sequence identity (i.e., 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to any strain and/or serovar of *H. parasuis* currently known or later discovered or developed, such as, but not limited to, strains identified by the GenBank Accession numbers NZ_CP015099.1, NZ_CP009237.1, or NZ_CP009158.1, and/or by SEQ ID NO: 4, SEQ ID NO: 5, or SEQ ID NO: 6, and particularly serovars 2, or 7. In some embodiments, the one or more antigens from *A. suis* comprise one or more antigens having at least a 85% sequence identity (i.e., 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to any strain and/or serovar of *A. suis* currently known or later discovered or developed, such as, but not limited to, the strain identified by the GenBank Accession number NZ_CP009159.1 and/or by SEQ ID NO: 7.

In some embodiments, the one or more antigens from SIV may comprise one or more antigens having at least a 85% sequence identity (i.e., 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to any strain of SIV, such as, but not limited to, identified by GenBank Accession numbers M81707, KC676310.1, AF222769, JQ783083.1, KU942624.1, AF268128, AF268124, KP788773.1, KU229931, CY158137, and/or by SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. In some embodiments, the one or more antigens from PEDV may comprise one or more antigens having at least a 85% sequence identity (i.e., 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to any strain of PEDV, such as, but not limited to, SEQ ID NO: 18, SEQ ID NO: 19, SEQ ID NO: 20, SEQ ID NO: 21, SEQ ID NO: 22, SEQ ID NO: 23, SEQ ID NO: 24, or SEQ ID NO: 25. In some embodiments, the one or more antigens from PRRSV may comprise one or more antigens having at least a 85% sequence identity (i.e., 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100%) to any strain of PRRSV, such as, but not limited to, SEQ ID NO: 26, SEQ ID NO: 27, SEQ ID NO: 28, SEQ ID NO: 29, or SEQ ID NO: 30.

In some embodiments, the inactivated antigens include, but are not limited to, whole culture bacteria; subunits obtained from the *S. suis, A. suis* and/or *H. parasuis*, and/or from any other bacteria or virus that may be included, that have been extracted or separated from the culture; subunits that have been extracted or separated from the cells; antigens obtained from recombinant organisms other than *S. suis, A. suis* or *H. parasuis* but which protect against *S. suis, A. suis* or *H. parasuis* infection or challenge; or combinations thereof. Such antigens may also be combined with other antigens that are typically administered to subjects, such as pigs, particularly neonatal pigs. Such additional antigens include, but are not limited to, antigens from *M. hyorhinis, M. hyosynoviae, P. multocida, B. bronchiseptica, E. rhusiopathiae, S. cholerasuis, S. typhimurium, E. coli, C. perfringens, C. difficile*, porcine rotaviruses swine influenza virus (swine influenza virus, SIV), porcine reproductive and respiratory syndrome virus (PRRSv), porcine epidemic diarrhea virus (PEDv), porcine parvo virus, or a combination thereof, and/or others known to persons of ordinary skill in the art.

In some embodiments, the inactivated antigens include, but are not limited to, whole culture viruses; subunits or recombinants obtained from SIV (IAV-S), PRRSv, PEDV and/or from any other virus that may be included, that have been extracted or separated from the culture; subunits that have been extracted or separated from the cells; antigens obtained from recombinant organisms other than SIV (IAV-S), PRRSv and PEDV but which protect against swine influenza, PRRSv or PEDV infection or challenge; or combinations thereof. Such antigens may also be combined with other antigens that are typically administered to subjects, such as pigs, particularly neonatal pigs. Such additional antigens include, but are not limited to, antigens from porcine rotaviruses, porcine parvo virus, or a combination thereof, and/or others known to persons of ordinary skill in the art or any bacterial antigens such as *M. hyorhinis, M. hyosynoviae, P. multocida, B. bronchiseptica, E. rhusiopathiae, S. cholerasuis, S. typhimurium, E. coli, C. perfringens, C. difficile*, or a combination thereof.

In some embodiments, the composition does not comprise a nanoparticle. In some embodiments, the composition does not comprise a nanoparticle that comprises one or more biodegradable polymers.

In some embodiments, administering the composition mucosally, such as intranasally, to a neonatal pig results in an IgA immune response that also may help to overcome maternal antibodies that the piglet may receive from a sow or gilt that is positive for *S. suis, H. parasuis, A. suis*, SIV (IAV-S), PRRSv, PEDV, rotavirus or any other bacteria or virus. If the neonatal pig receives maternal antibodies and then receives a parenteral vaccination, the maternal antibodies often block the neonate from developing its own protective antibodies. The method of mucosal vaccination, such as intranasal, administration described herein may produce an IgA response that can help overcome the maternal antibodies transferred to neonates.

Immunogenic compositions for mucosal administration, such as intranasal administration, have several advantages over compositions that are administered by other routes, such as the intramuscular or subcutaneous routes. The advantages include, but are not limited to: 1) protecting the neonatal pigs using humane techniques; 2) not exposing the neonate to stressful needle injections; 3) not involving injecting the neonates with live or modified live organisms that can shed and spread disease; 4) allowing the neonate to develop IgA antibodies that can overcome maternal IgG antibodies transferred from the sow or gilt; 5) not leaving any injection site lesions and thus allowing a zero day withdrawal time; 6) being easier to administer and reducing the workload; 7) reducing or substantially eliminating the risk of accidental self-injection of the worker; and/or 8) being able to be administered in the face of an outbreak to stop disease spread in a herd. Other advantages may be apparent from the description and the example section below.

Embodiments of the composition may be able to provide better protection against diseases caused by *S. suis, A. suis, H. parasuis*, SIV (IAV-S), PRRSv, PEDV, rotavirus, and similar organisms that cause infections through the respiratory tract, following revaccination or additional administration of an immunogenic composition. The revaccination or additional administration may be delivered via the intranasal route or by a parenteral route such as intramuscular, subcutaneous or intravenous. Furthermore, the disclosed composition may also be able to overcome maternal antibody inhibition of piglet antibody production, thus providing a greater protection of neonatal pigs throughout their development, compared to neonatal pigs that are not administered the disclosed composition.

Some embodiments of the disclosed composition are able to induce protective levels of antibodies as measured by the ELISA in >50%, typically in >80% of the individuals that are administered the composition. In some embodiments, the mucoadhesive composition also is able to maintain protective levels of antibodies against the *S. suis, A. suis, H. parasuis*, SIV (IAV-S), PRRSv, PEDV and/or rotavirus strains throughout the piglet growth phase from the neonatal or pre-weaning phase through the nursery phase, which is typically from weaning at about 21 days of age to about 10 weeks of age. Thus, in certain embodiments, the composition can produce a persistent immune response against *S. suis, A. suis, H. parasuis*, SIV (IAV-S), PRRSv, PEDV and/or related diseases. As used herein, a "persistent immune response" refers to a protective antibody immune response which is capable of protecting the pigs throughout their growth period in the nursery.

Embodiments of the immunogenic composition that comprise one or more strains of inactivated *S. suis, A. suis* and/or inactivated *H. parasuis*, that are each independently grown to titers greater than $10^2$ CFU/mL, preferably greater than $10^5$ CFU/mL, and more preferably greater than $10^7$ CFU/mL, induce high titers of IgA antibodies in neonatal pigs. Such IgA titers measured in serum will be at least 50 ELISA units, preferably greater than 100 ELISA units.

Additional embodiments of the immunogenic composition that comprise one or more strains of inactivated SIV (IAV-S), including but not limited to H1N1 and H3N2, PRRSv, PEDV, and/or inactivated rotavirus, that are each independently grown to titers greater than $10^2$ $TCID_{50}$/mL, preferably greater than $10^5$ $TCID_{50}$/mL, induce high titers of IgA antibodies in neonatal pigs. Such IgA titers measured in mucosal washings or in serum will be at least 10 ELISA units, preferably greater than 50 ELISA units.

Figure 2:
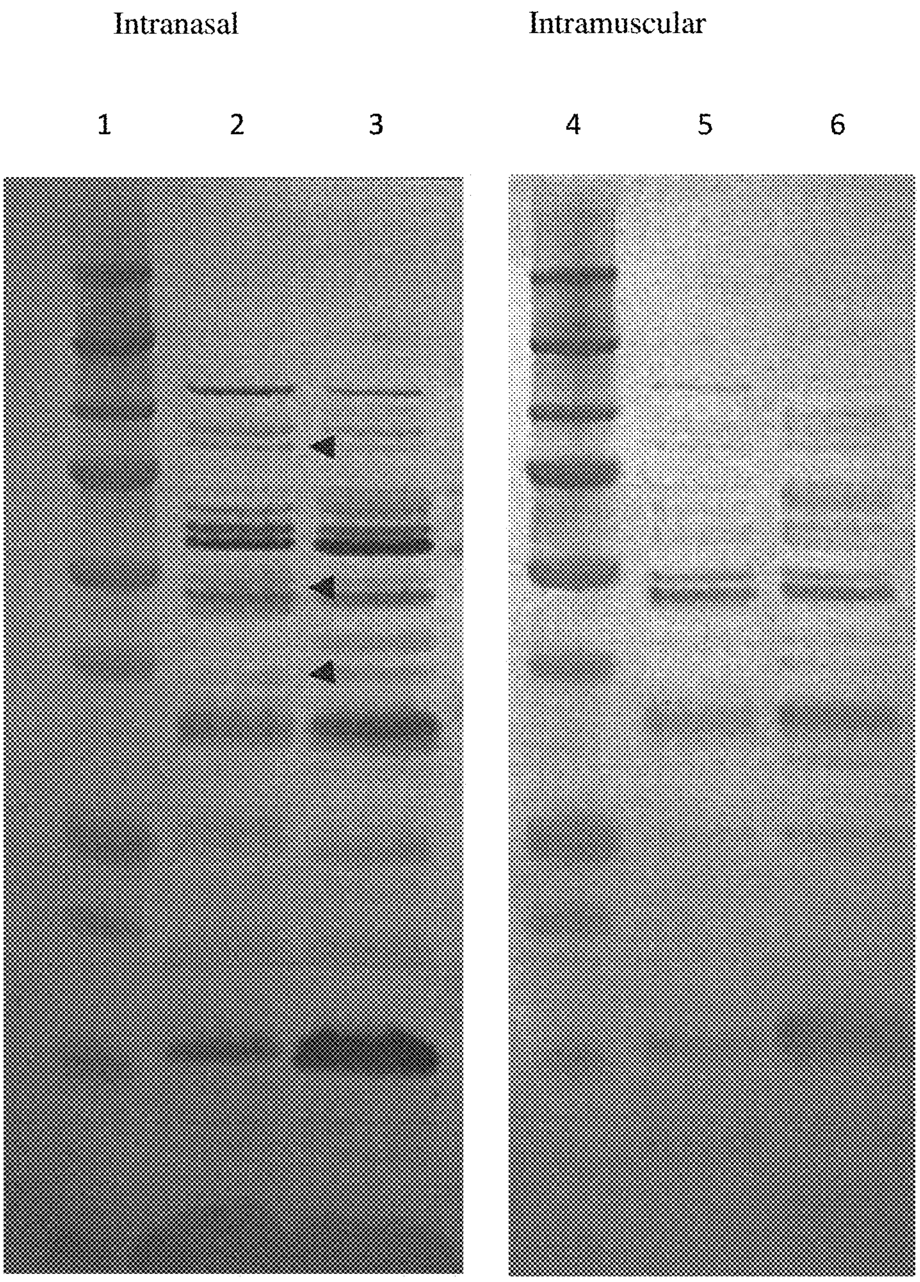
FIG. 2 is a Western Blot of *H. parasuis* antigens, comparing pig antibody responses produced by intranasal (lanes 1, 2, and 3) or intramuscular (lanes 4, 5, and 6) vaccination with a combination of inactivated *H. parasuis, A. suis*, and *S. suis*, establishing that intranasal administration resulted in protective antibody production in the pig.

Surprisingly, embodiments of the disclosed immunogenic composition, when delivered to neonatal pigs via the mucosal route, such as an intranasal route, also induced serum IgG responses as demonstrated in the piglets (see FIGS. 1 and 2 and Table 2). In some embodiments, such titers are from 0 to 50 ELISA units, but in other embodiments, the titers are greater than 50 ELISA units. It is expected that a mucosal IgA response will be measurable prior to the serum IgA response.

In some embodiments, the immunogenic composition comprises one or more strains or isolates of inactivated *S. suis*, one or more strains or isolates of *A. suis*, one or more strains or isolates of *H. parasuis*, one or more strains or subtypes of SIV (IAV-S), one or more isolates or groups of PRRSv, one or more isolates of PEDV and/or one or more isolates or types of rotaviruses which have been isolated from infected pigs. In such embodiments, the strains may not have been passaged in artificial culture (in vitro) more than 20 times. Preferably, the one or more strains of *S. suis, A. suis, H. parasuis* SIV (IAV-S), PRRSv, PEDV and/or rotavirus would not be passaged more than 10 times in vitro.

In some embodiments, the immunogenic composition is an inactivated vaccine.

The composition may be administered to a subject, such as a pig, of any age. In some embodiments, the initial administration is to pigs of from birth to 10 days of age, such as from one to ten days of age, from one to five days of age, or from one to three days of age. One or more additional administrations of a composition comprising one or more inactivated antigens obtained from one or more strains of *S. suis, A. suis, H. parasuis*, SIV (IAV-S), PRRSv, PEDV, and/or rotavirus may be necessary in two to six weeks from the initial administration of the disclosed composition. This second administration may be delivered parenterally and may include non-mucoadhesive adjuvants. Any additional administrations may be administered via a mucosal route, such as intranasal, or any other route that is preferred by the administrator. For instance, the additional administrations may be mucosal such as intranasal, intramuscular, subcutaneous, intraperitoneal, intravenous, or a combination thereof.

III. Examples

Example 1—Composition Preparation

Two compositions were prepared for vaccination of neonates farrowed to sows in the farm described in Example 2. The object was to determine whether intranasal administration of the disclosed composition to neonates within the first five days of life would help to reduce morbidity and mortality among the pigs. Multiple isolates of *S. suis* (serovars ½, 2, and 3) and *H. parasuis* (serovars 2, 7, and non-typeable) and one isolate of *A. suis* were identified and found to be responsible for causing clinical disease and mortality in the nursery pigs. Bacterins (inactivated bacterial vaccines) were prepared by growing all of the isolates in vitro to titers $>10^5$ CFU/mL. Each isolate was inactivated with 0.1% formalin after which isolates were pooled in equal amounts. After pooling, the pool was split into two equal aliquots. One aliquot was first adjuvanted with 4% aluminum hydroxide. This was followed by adding an oil-in-water adjuvant called Emulsigen® at 12% v/v. The second aliquot was adjuvanted with 10% Carbigen™, a mucoadhesive polyacrylic acid adjuvant.

Example 2—Experimental Design

A commercial sow farm of 2,000 sows experiencing significant nursery mortality from *S. suis, A. suis* and/or *H. parasuis* infection was selected for evaluation of the different administration routes/regimens of piglets. Nursery pigs from this source were also positive for porcine reproductive and respiratory syndrome virus (PRRS), porcine circovirus type 2 (PCV2), swine influenza A (IAV-S), and *M. hyopneumoniae*. Pigs were weaned at 21 days of age and transferred to a single-source, off-site nursery. The nursery contained four rooms which were filled with approximately 900 pigs each. When clinical disease occurred in the nursery, individual animals were given an antibiotic injection. No feed or mass water medications were administered.

Neonatal piglets were enrolled at the sow farm into the study over five consecutive weeks of farrowing. Administration occurred at the time of processing which was between the third and fifth day post farrowing. The piglets were randomly assigned to one of four groups by colored ear tags. The groups are shown in Table 1 and were:

1) intranasal (IN) administration at processing and repeated at weaning (about 21 days of age);

2) IN administration at processing and intramuscular (IM) injection at weaning;

3) IM administration at processing and repeated at weaning; and

4) IN administration at processing only (a single administration of the composition).

Piglets within litters were placed in different groups so as to equally represent each of the four treatment groups as much as possible. At weaning, treatment groups of pigs were not sorted to separate pens. The animals were randomly mixed together in order to promote uniform exposure to pathogens.

TABLE 1

Administration adjuvants and regimes

| Group No. | Adjuvant | Routes of Administration | Dose Size (mL) | No. of Doses | No. of Piglets | Age at administration (Days) |
|---|---|---|---|---|---|---|
| 1 | Carbigen ™ | IN/IN | 2.0 | 2 | 911 | 3-5/21 |
| 2 | Carbigen ™/Emulsigen ® + Aluminum hydroxide | IN/IM | 1.0/2.0 | 2 | 911 | 3-5/21 |
| 3 | Emulsigen ® + Aluminum hydroxide | IM/IM | 2.0/2.0 | 2 | 929 | 3-5/21 |
| 4 | Carbigen ™ | IN | 1.0 | 1 | 848 | 3-5 |

Example 3—Laboratory Testing

From pigs in the week 3 production group, 10 serum samples were randomly collected from each of the four treatment groups at approximately three weeks after the weaning administrations. The samples were analyzed by homologous ELISA using soluble proteins obtained from the *H. parasuis* vaccine strains as coated antigens in an assay method described by Lin, B. et al. "Antibody response of young pigs to autogeneous *Haemophilus parasuis* vaccine," AASV 2007:207. IgA and IgG in serum samples were measured and are shown in Table 2 and FIG. 1.

The majority of animals in each of the treatment groups in this investigation responded with measurable ELISA IgA titers to *H. parasuis* (vaccine strain) indicating that the pigs had largely (>80%) seroconverted. The IN/IM and IM/IM groups were the only treatments that resulted in >80% rate of seroconversion as measured by IgG titer. Surprisingly, the IN groups developed significant IgG ELISA titers in the serum.

TABLE 2

IgA and IgG Antibody responses post administration

| Group | Routes of | Antibody Response to *H. parasuis* as measured by ELISA | |
|---|---|---|---|
| No. | Administration | IgA | IgG |
| 1 | IN/IN | 320 | 60 |
| 2 | IN/IM | 220 | 540 |
| 3 | IM/IM | 580 | 560 |
| 4 | IN Single Dose | 140 | 260 |

Example 4—Western Blot Analysis of Antibody Response to Antigens of *H. Parasuis*

Blood samples were obtained randomly from 10 pigs in each of the IN/IN and IM/IM groups of pigs from Example 2. Equal aliquots were pooled and were used in a Western Blot analysis to evaluate the antibody responses of pigs to antigens of *H. parasuis* known to be important for protection. FIG. 2 provides the Western Blot for the IN/IN and IM/IM groups, with lanes 1, 2 and 3 representing the IN/IN group, and lanes 4, 5 and 6 representing the IM/IM group. Lanes 1 and 4 are molecular weight markers (Bio-Rad #161-0373); lanes 2 and 5 are loaded with 20 ug/well of Hps #32575; and lanes 3 and 6 are loaded with 20 ug/well of Hps #31136.

The Western Blot analysis demonstrated that the IN/IN group of pigs developed significant antibody responses to all of the important protective antigens of both *H. parasuis* strains that were included in the inactivated vaccine that they received (FIG. 2). From top to bottom, the arrows in FIG. 2 indicate the presence of the bands at 82 kD (neurimidase), 48 kD (P2 adhesion protein) and the 35 kD outer membrane protein, illustrating the presence of important antigens in the IN/IN group. Surprisingly, the IN/IN group developed stronger antibody responses than the pigs in the IM/IM group.

Example 5—Results of Herd Administration

Over the five weeks of study observation, the parameters recorded were pre-weaning mortality, percent nursery mortality, percent treated animals (antibiotic injected upon presence of clinical disease), and the percent poor quality pigs at the end of the nursery phase.

Data collected by treatment group for production week one through four were statistically analyzed. The week of production was used as the experimental unit. Main effects ANOVA was performed with percent nursery mortality, total percent mortality (pre-weaning mortality plus nursery mortality), percent treated animals, and percent poor quality pigs as the dependent variables and administration treatment as the independent variable.

As noted in Table 3, during the nursery phase the IN/IN and IN/IM groups had average mortality of 3.70% (s.d. 2.77%) and 9.13% (s.d. 6.67%), respectively. The average mortality observed in the IM/IM group was 5.03% (s.d. 3.49%) whereas the average mortality observed in the IN single dose (only once at processing) group was 1.42% (s.d. 1.79%). Statistical analysis indicated that across treatments, the type of administration did not significantly affect the mortality rate in the nursery ($p>0.05$). However, there is a strong indication that the single intranasal vaccination produced the best result with the IN/IN vaccination regimen producing the second best result.

TABLE 3

Average mortality during the nursery phase

| Group No. | Routes of Administration | Percent Mortality | Standard Deviation |
|---|---|---|---|
| 1 | IN/IN | 3.70 | 2.77 |
| 2 | IN/IM | 9.13 | 6.67 |
| 3 | IM/IM | 5.03 | 3.09 |
| 4 | IN (single dose) | 1.42 | 1.79 |

For total mortality (Table 4) which included both the pre-weaning and nursery mortality observed, the IN/IN and IN/IM groups had average mortality of 12.7% (s.d. 2.61%)

and 14.5% (s.d. 7.68%), respectively. The IM/IM group was 12% (s.d. 3.67%) whereas the average total mortality observed in the IN (single dose at processing age of 3-5 days) group was 11.3% (s.d. 1.58%). Across treatments, a single dose of vaccine administered intranasally at processing was as effective as two doses administered IN/IN, IN/IM or IM/IM (p>0.05). These results indicate that the greatest mortality occurred during the pre-weaning phase rather than the nursery phase.

TABLE 4

Average total mortality during both the pre-weaning and nursery phases

| Group No. | Routes of Administration | Percent Mortality | Standard Deviation |
|---|---|---|---|
| 1 | IN/IN | 12.7 | 2.61 |
| 2 | IN/IM | 14.5 | 7.68 |
| 3 | IM/IM | 12.0 | 3.67 |
| 4 | IN (single dose) | 11.3 | 1.58 |

Table 5 shows the percentage of piglets treated with antibiotics. The IN/IN and IN/IM groups had an average treatment mortality rate of 8.78% (s.d. 3.84%) and 9.53% (s.d. 6.17%), respectively. The IM/IM group was 7.63% (s.d. 3.53%) while the average treatment rate observed in the IN (only at processing) group was 6.88% (s.d. 4.82%). Again, piglets receiving a single intranasal administration at 3-5 days of age or intranasal administration at 3-5 days of age followed by a second intranasal administration at weaning (about 21 days) required no more antibiotic treatments than piglets receiving regimens including intranasal administration followed by intramuscular or two intramuscular administration (p>0.05).

TABLE 5

Percentage of piglets treated with antibiotics during the study

| Group No. | Routes of Administration | Percent Mortality | Standard Deviation |
|---|---|---|---|
| 1 | IN/IN | 8.78 | 3.84 |
| 2 | IN/IM | 9.53 | 6.17 |
| 3 | IM/IM | 7.83 | 3.53 |
| 4 | IN (single dose) | 6.88 | 4.82 |

For nursery pigs grading as poor quality (see Table 6), the IN/IN and IN/IM groups had average poor quality of 22.60% (s.d. 4.91%) and 24.53% (s.d. 8.39%), respectively. "Poor quality" was defined as any pig that could be downgraded for any reason (for example, lighter weight). The IM/IM group was 22.65% (s.d. 6.02%) whereas the rate of poor quality pigs observed in the IN (only at processing) group was 22.23% (s.d. 11.63%). Across treatments, the type of administration did not significantly affect the percentage of poor quality pigs observed at the end of the nursery phase (p>0.05).

TABLE 6

Percentage of poor quality piglets in the nursery

| Group No. | Routes of Administration | Percent Mortality | Standard Deviation |
|---|---|---|---|
| 1 | IN/IN | 22.60 | 4.91 |
| 2 | IN/IM | 24.53 | 8.39 |

TABLE 6-continued

Percentage of poor quality piglets in the nursery

| Group No. | Routes of Administration | Percent Mortality | Standard Deviation |
|---|---|---|---|
| 3 | IM/IM | 22.65 | 6.02 |
| 4 | IN (single dose) | 22.23 | 11.63 |

In summary, the nursery performance for the parameters measured, demonstrated that a single intranasal dose administered at 3-5 days of age or two intranasal doses administered at 3-5 days of age and again at about 21 days of age were as effective as regimens that included intramuscular administration. However, the intranasal administration has additional advantages over intramuscular administration, including not involving stressful needle injections to neonatal pigs, not involving injecting the neonates with live or modified live organisms that can shed and spread disease, not leaving any injection site lesions and thus allowing a zero day withdrawal time, and being easier to administer and thus reducing the workload and worker's risk of accidental self-injection for those administrating the composition. Furthermore, the intranasal administration may result in the neonate developing IgA antibodies that can overcome maternal IgG antibodies that are transferred from the sow or gilt.

Example 6—Swine Influenza Virus

Introduction

Swine influenza is an acute, highly contagious, respiratory disease resulting from type A swine influenza virus (SIV, also identified as IAV-S) infection. SIV is the leading cause of disease on swine farms in the US, affecting 61.5% of wean-to-finish farms, 59.4% of grower/finisher farms, 46.2% of nursery farms, and 25.5% of sow farms. It has been estimated total economic damage of $1.3 billion between May and October of 2009 caused by the SIV epidemic in the US. Financial losses attributable to SIV were estimated by one US swine producer at $10.31 per market pig. Vaccination is the main method of SIV prevention in pigs, with primary vaccination consisting of 2 injections 2 to 4 weeks apart, with biannual booster vaccinations recommended for sows. Unlike for other swine diseases, such as leptospirosis and *Erysipelothrix*, where vaccination levels on US breeding farms approach 90%, typically only 46.4% of breeding farms vaccinate female pigs for SIV.

Adjuvants are substances that, when mixed with an antigen, enhance its immunogenicity. Adjuvants are often used to boost the immune response when an antigen has low immunogenicity or when only small amounts of the antigen are available. For example, the antibody response of mice to immunization with bovine serum albumin (BSA) can be increased fivefold or more if the BSA is administered with an adjuvant. Adjuvants function by prolonging antigen persistence, enhancing costimulatory signals, causing higher local inflammation, stimulating the nonspecific proliferation of lymphocytes, or by performing a combination of the above. Good adjuvants can enable a reduction of the dose or the concentration of the antigen within a vaccine, decreasing the cost of the vaccine. All data indicate that the selection of the appropriate adjuvant as well as the mass of antigen, both of which differ between commercial vaccines, are at least as important for the potency of SIV vaccines as the selection of the SIV strains in the vaccines.

Emulsion-based adjuvant systems have been widely utilized in vaccine formulation. Several different classes of emulsions exist, such as oil-in-water (O:W) emulsions, water-in-oil (W:O) emulsions, water-in-oil-in-water (W:O:W) emulsions, and protein-stabilized emulsions. Water-in-oil-in-water emulsions contain water droplets within larger oil droplets, which are themselves suspended within a bulk aqueous solution. Whereas O:W emulsions are generally preferred for human applications, both W:O:W and W:O emulsions are widely used in veterinary vaccines. The advantages offered by W:O:W emulsions are their low viscosity as well as their ability to enhance the short and long term immune responses. Oil-adjuvanted vaccines significantly increase humoral immunity and generate higher antibody formation.

Typically, a hemagglutination inhibition (HI) titer of >1:40 is considered protective for SIV. However, it has been reported that vaccination with an inactivated SIV vaccine in pigs does not consistently generate complete immunity to virus challenges. The purpose of these experiments was to: 1) determine which MVP adjuvant would provide the optimal serological response when using inactivated SIV as the antigen; 2) evaluate whether a higher adjuvant concentration would produce greater antibody responses to SIV; 3); evaluate the effectiveness of a nanoparticle adjuvant delivered intramuscularly; and 4) determine which MVP adjuvant could produce antibody responses equivalent to or greater than an adjuvant included in one commercially available SIV vaccine for pigs.

Materials and Methods

Forty mixed sex commercial crossbreed swine of approximately 2 months of age were used and identified with identical numbered ear tags in each ear. Pigs were allowed to acclimate to the research facility for 3 days after placement at the research facility prior to initiating the trial. Five pigs were randomly allocated to each of 8 treatment groups (TGs), as per the rubric in Table 7. FluSure XP SIV vaccine (Zoetis, Inc.; Serial number: A283483A/A280666; Expiration date: Dec. 3, 2013; Lot number: 1285595) antigen was used as the antigen for this experiment. This antigen is an inactivated SIV that is lyophilized and provided separately from its commercial adjuvant.

TABLE 7

Experiment 1 Design

| TG Number[1] | Adjuvant | Lot Number | Number of Pigs |
|---|---|---|---|
| 1 | Negative control; PBS | 571 | 5 |
| 2 | Commercially available SIV vaccine adjuvant | 1285595 | 5 |
| 3 | Emulsigen ®-D 20% formulation | D1368 | 5 |
| 4 | Emulsigen ®-D 30% formulation | D1368 | 5 |
| 5 | Nanomune ™ 20% formulation | 062612 | 5 |
| 6 | Nanomune ™ 30% formulation | 062612 | 5 |
| 7 | Emulsigen ®-DL90 20% formulation | 062613 | 5 |
| 8 | Emulsigen ®-DL90 30% formulation | 062613 | 5 |

[1]TG = Treatment group; PBS = Phosphate buffered saline.

For all O:W emulsion adjuvants (Emulsigen®-D, Emulsigen®-DL90 and Nanomune), the lyophilized antigen was reconstituted to the labeled volume with sterile distilled water (DI) containing the concentration of adjuvant noted in Table 7. For the commercially available inactivated SIV vaccine, the adjuvanted diluent sold with the product was used to reconstitute the SIV antigen. Treatment Group 1 served as a negative control group, and received an identical injection of phosphate buffered saline instead of receiving SIV antigen or adjuvant. A 2 mL dose containing vaccine plus adjuvant was injected into each pig intramuscularly in the right side of the neck. The adjuvant that each TG received was as follows: TG 1: PBS as negative control (Lot number: 571); TG 2: adjuvant included in a commercially available SIV vaccine; TG 3: Emulsigen®-D formulated with antigen at a 20% concentration (MVP Adjuvants; Lot number: D1368); TG 4: Emulsigen®-D formulated with antigen at a 30% concentration (MVP Adjuvants; Lot number: D1368); TG 5: Nanomune, a nanoparticle adjuvant, formulated with antigen at a 20% concentration (MVP Adjuvants; Lot number: 062612); TG 6: Nanomune formulated with antigen at a 30% concentration (MVP Adjuvants; Lot number: 062612); TG 7: Emulsigen®-DL90 formulated with antigen at a 20% concentration (MVP Adjuvants; Lot number: 062613); TG 8: Emulsigen®-DL90 formulated with antigen at a 30% concentration (MVP Adjuvants; Lot number: 062613).

All pigs received 2 doses of vaccine and adjuvant based on their respective TGs; 1 dose on study day (D) 0, and 1 dose on D 21. Five to 10 mL of venous blood was drawn from each pig at 3 time points; on D 0, prior to immunization; on D 21, prior to immunization, and on D 42. Blood samples from each time point were split into 2 equal aliquots. One aliquot from each blood sampling day was used to test immunity using the HI assay by the Iowa State University (ISU) Veterinary Diagnostic Laboratory (VDL). Statistical analysis of serum antibody levels in this experiment was performed using repeated measures analysis of variance.

Results and Discussion

Figure 3:
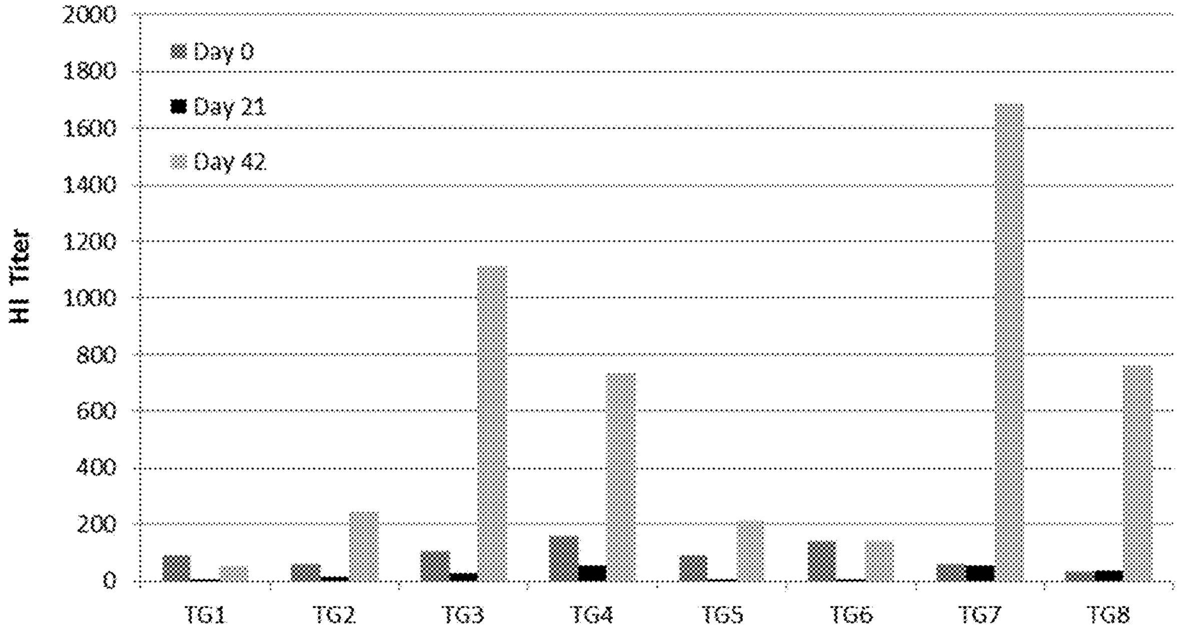
FIG. 3 is a graph of Hemagglutination inhibition (HI) titer versus treatment group (TG), illustrating the HI titers by treatment group for H1N1 swine influenza virus in Example 6.
Figure 4:
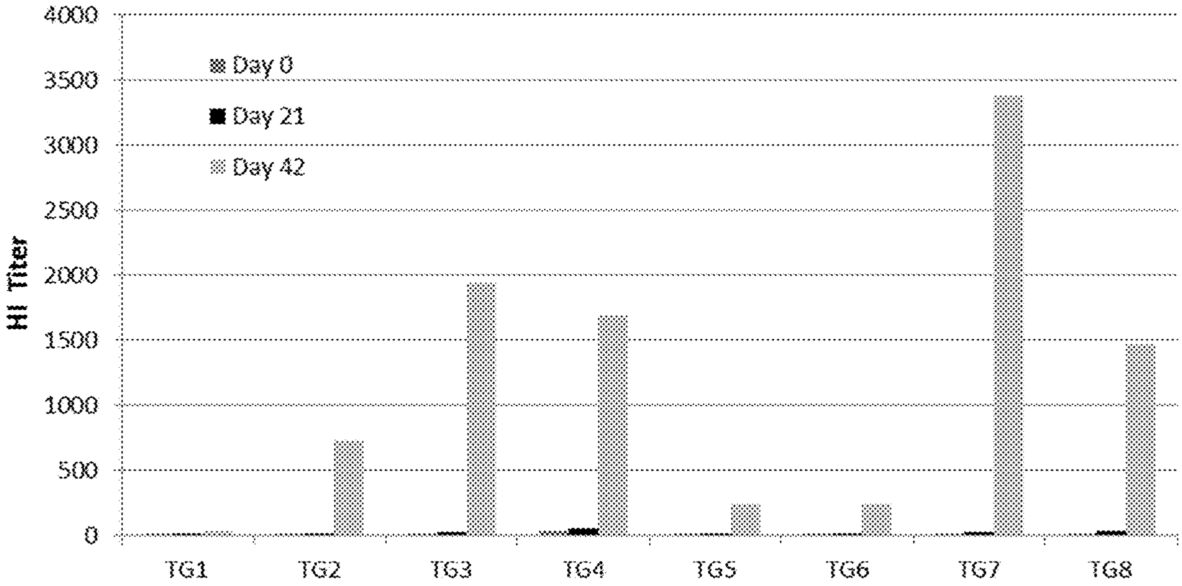
FIG. 4 is a graph of HI titer versus treatment group, illustrating the HI titers by treatment group for H3N2 swine influenza virus in Example 6.

The results from this experiment are presented graphically in FIGS. 3 and 4. On Day 0, prior to vaccination, several HI antibody titers were positive, probably due to maternal antibody. Maternal SIV antibody levels are dependent on antibody levels in the sow and decline in piglets over a period of 4-14 weeks. It is noted that the TG1 titers declined from Day 0 to Day 42 so there was no SIV exposure during the study.

On D 21, using 1:40 as a cut-off point for successful generation of protective immunity to SIV, several pigs in the Emulsigen®-DL90 and the Emulsigen®-D treatment groups (TG 3, 4, 7, and 8) already possessed protective HI antibody levels against SIV. On Day 21, for the H1N1 strain of SIV, 20% of pigs in TG 3, 80% of pigs in TG 4, 80% of pigs in TG 7, and 60% of pigs in TG 8 possessed protective HI antibody levels whereas 0% of the pigs in TG groups 1, 2, 5 and 6 demonstrated such titers. On Day 21, for the H3N2 strain of SIV, 20% of pigs in TG 3, 80% of pigs in TG 4, 20% of pigs in TG 7, and 60% of pigs in TG 8 possessed protective HI antibody levels whereas 0% of the pigs in TG groups 1, 2, 5 and 6 demonstrated protective HI antibody titers whereas. Earlier generation of protective immunity ensures that pigs will be protected in the event they face a disease challenge prior to receiving both doses of vaccine. Additionally, these results indicate that even in the presence of maternal antibody, Emulsigen®-D and Emulsigen®-DL90 could produce protective titers at 21 days post a single vaccination.

Statistics

On Day 42, all pigs in all immunized treatment groups, TG 2-8, had protective levels of antibody for both the H1N1 and the H3N2 strains of SIV. Emulsigen®-DL90 produced higher antibody titers than any other adjuvant tested in this experiment, indicating the generation of the highest level of protective immunity of all adjuvants tested in this experiment. Emulsigen®-D also produced very high antibody titers, more than four-fold higher than the antibody titers produced by the adjuvant from a commercially available SIV vaccine (TG 2). Generation of higher antibody titer levels enables using lower levels of antigen, helping to reduce vaccine costs.

In this experiment, 3 of the analyzed adjuvants were tested at 2 different formulation concentrations, 20% and 30%. For all 3 of these adjuvants, the lower 20% concentration yielded higher antibody levels than did the 30% concentration. Adsorption of adjuvant to antigen is determined in part by the adjuvant:antigen ratio. Without being bound to a particular theory, an intermediate density of ligands, such as adjuvants, may provide statistically significant improvements in cell binding in comparison with both higher and lower densities of adjuvants. Higher adjuvant densities may bind and mask too many antigen receptors, lowering the number of antigen receptors available to bind host cells involved in the immune response and production of antibody, explaining the lower antibody titers noted when using a higher concentration of adjuvant.

Nanomune, a nanoparticle adjuvant, produced very low antibody titers. Adjuvants adsorb antigens and serve as a depot at the site of vaccine injection, slowly releasing antigen into the body, thereby allowing antigen-specific lymphocytes to be exposed to antigen for a longer period of time. Nanoparticles, due to their small size, may diffuse from the site of injection more quickly, resulting in less exposure to antigen-specific lymphocytes, and hence generation of lower levels of antibody. Further, adjuvant-antigen complexes involving nanoparticles are smaller than adjuvant-antigen complexes involving larger-sized adjuvants, lowering the likelihood of phagocytosis, in turn lowering the overall immune response and lowering antibody level.

Example 7

This experiment was performed identically to the experiment described in Example 6, except that it utilized different TGs receiving different adjuvants. Pigs were allocated to each of 8 TGs, as per the rubric in Table 8. Five pigs were allocated to TG 1-5 and TG 8. Ten pigs were allocated to each of groups TG 6 and TG 7. Serum was collected from all pigs on D 0, D 21 and D42.

TABLE 8

Experiment 2 Design

| TG Number[1] | Adjuvant | Lot Number | Administration[2] | Number of Pigs |
|---|---|---|---|---|
| 1 | Negative control; PBS | 598 | IM on D 0, D 21 | 5 |
| 2 | Commercially available SIV vaccine adjuvant | 1312332 | IM on D 0, D 21 | 5 |
| 3 | Emulsigen ®-D 20% | D1384 | IM on D 0, D 21 | 5 |
| 4 | Emulsigen ®-DL90 20% | 062014B | IM on D 0, D 21 | 5 |
| 5 | Emulsigen ®-BCL 20% | 17007 | IM on D 0, D 21 | 5 |
| 6 | Seppic W:O:W 50% | 082814S | IM on D 0, D 21 | 10* |
| 7 | MVP W:O:W 20% | 082814M | IM on D 0, D 21 | 10* |
| 8 | Carbigen ™ 10% | 18053 | Intranasally D 0, D 21 | 5 |

[1]TG = Treatment group; PBS = Phosphate buffered saline; DDA = dimethyldioctadecylammonium bromide; W:O:W = Water-in-oil-in-water immersion; IM = intramuscular; D = Study day.
[2]All IM injections administered in the right side of the neck; IM injections administered as a 2 mL dose; Intranasal administration was 1 mL in each nostril, for a total dose of 2 mL.
*10 pigs total were included in TG 6 and TG 7.

FluSure XP SIV vaccine (Zoetis, Inc.; Serial number: A309195/A310732; Expiration date: Mar. 3, 2015; Lot number: 1312332) an inactivated, lyophilized antigen was used as the antigen for this experiment. This antigen was mixed as follows with a different adjuvant for each TG. For all O:W emulsion adjuvants (Emulsigen®-D, Emulsigen®-DL90 and Emulsigen®-BCL), the lyophilized antigen was reconstituted to the labeled volume with sterile distilled water (DI) containing the concentration of adjuvant noted in Table 8. For the commercially available SIV vaccine, the adjuvanted diluent sold with the antigen was used to reconstitute the SIV antigen. For the Seppic W:O;W emulsion (ISA 201) adjuvant, SIV antigen was reconstituted with 50% of the required diluent as PBS and the ISA 201 was added at a 50% concentration according to directions provided by the manufacturer. For the MVP W:O:W emulsion adjuvant, SIV antigen was reconstituted with 80% of the required diluent after which the MVP W:O:W emulsion was added at a 20% concentration. For the Carbigen™ adjuvant, the adjuvant was first added to the required volume of PBS, the pH was adjusted to between 6.0 and 6.5 using 10N NaOH and then this was used to reconstitute the lyophilized SIV antigen to the concentration listed in Table 8.

Treatment Group 1 served as a negative control group, and received an identical injection of PBS instead of receiving SIV antigen or adjuvant. The adjuvant that each TG received was as follows: TG 1: PBS as negative control (Lot number: 598); TG 2: adjuvant included in a commercially available SIV vaccine; TG 3: Emulsigen®-D formulated at 20% with DDA (MVP Adjuvants; Lot number: D1384); TG 4: Emulsigen®-DL 90 formulated at 20% with DDA (MVP Adjuvants; Lot number: 062014B); TG 5: Emulsigen®-BCL formulated at 20% (MVP Adjuvants; Lot number: 17007); TG 6: Seppic W:O:W formulated at 50% (MVP Adjuvants; Lot number: 082814S); TG 7: MVP W:O:W formulated at 20% (MVP Adjuvants; Lot number: 082814M); TG 8: Carbigen™ formulated at 10% (MVP Adjuvants; Lot number: 18053).

A 2 mL dose containing vaccine plus adjuvant was injected into each pig intramuscularly in the right side of the neck for TGs 1-7. Treatment group 8 received a 2 mL dose containing vaccine plus adjuvant administered intranasally, with 1 mL administered into each nostril. All pigs received 2 doses of vaccine and adjuvant; 1 dose on D 0, and 1 dose on D 21. Blood sampling and analysis was the same as described for experiment 1 above. Statistical analysis of serum antibody levels in this experiment was performed using repeated measures analysis of variance.

All serum samples were split into two aliquotes. One aliquot was sent to Iowa State University diagnostic laboratory for testing of hemagglutination inhibition titers. Samples were blinded as per group and sampling day. Geometric mean data were analyzed statistically using repeated measures analysis of variance.

Results and Discussion

Figure 5:
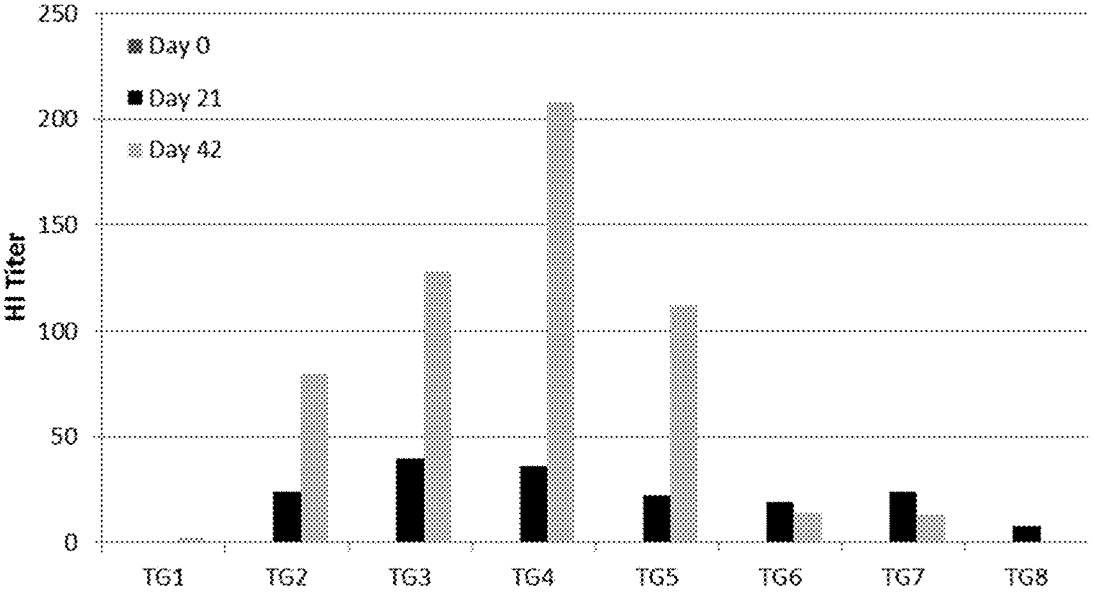
FIG. 5 is a graph of Hemagglutination inhibition (HI) titer versus treatment group (TG), illustrating the HI titers by treatment group for H1N1 swine influenza virus in Example 7.
Figure 6:
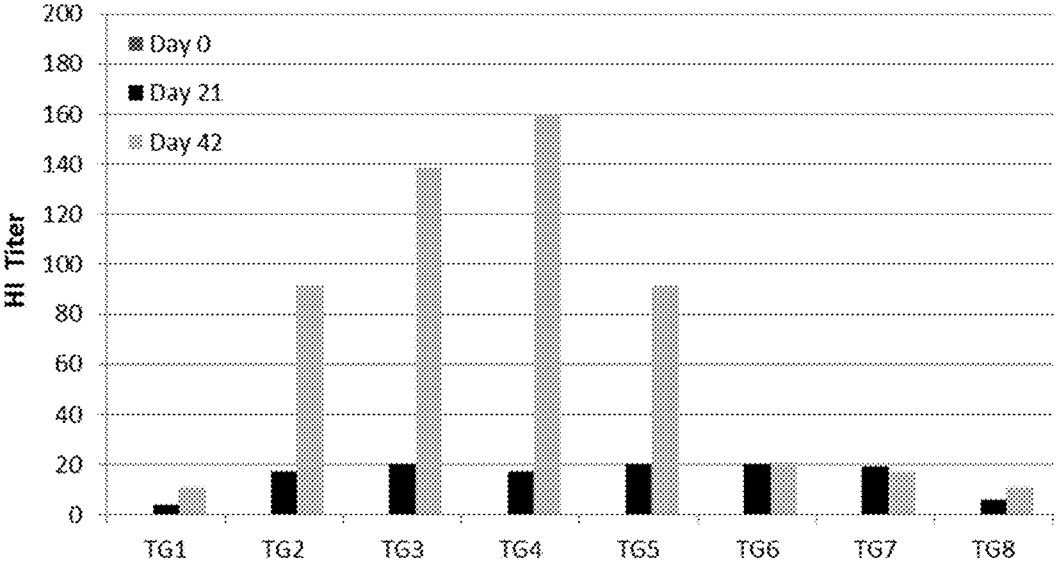
FIG. 6 is a graph of HI titer versus treatment group, illustrating the HI titers by treatment group for H3N2 swine influenza virus in Example 7.
Figure 7:
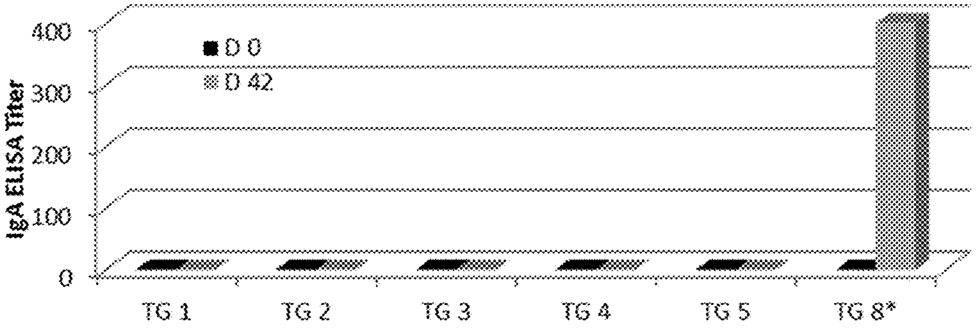
FIG. 7 is a graph of IgA ELISA titers versus treatment group, illustrating the IgA titers for the various treatment groups in Example 7.

The results from this experiment are presented graphically in FIGS. 5-7, and in Tables 9 and 10.

TABLE 9

| Hemagglutination Inhibition IgG Titers | | | | | | |
|---|---|---|---|---|---|---|
| | Day 0 | | Day 21 | | Day 42 | |
| Adjuvant | H1N1 | H3N2 | H1N1 | H3N2 | H1N1 | H3N2 |
| No Adj | 0 | 0 | 0 | 0 | 2.5 | 12.5 |
| Amphigen | 0 | 0 | 24 | 24 | 80 | 96 |
| EM-D 20% | 0 | 0 | 40 | 40 | 128 | 144 |
| EM-DL90 20% | 0 | 0 | 36 | 36 | 208 | 192 |
| EM-BCL 20% | 0 | 0 | 22 | 22 | 112 | 96 |
| SEPPIC WOW 20% | 0 | 0 | 19 | 19 | 14 | 22 |
| MVP WOW 20% | 0 | 0 | 24 | 24 | 13 | 18 |
| Carbigen 10% | 0 | 0 | 8 | 0 | 0 | 12 |

TABLE 10

| SIV Specific IgA response as measured by ELISA | | |
|---|---|---|
| IgA | Day 0 | Day 42 |
| Control | 0 | 0 |
| Amphigen | 0 | 0 |
| EMULSIGEN-D | 0 | 0 |
| EMULSIGEN-DL90 | 0 | 0 |
| EMULSIGEN-BCL | 0 | 0 |
| CARBIGEN-IN | 0 | 400 |

In this experiment, no positive antibody titers were found on Day 0, prior to immunization, indicating the lack of any maternal antibody, enabling definitive determination that all detected antibody resulted from immunization and not from any minor lingering levels of maternal antibody. On Day 21, for the H1N1 strain of SIV, 20% of pigs in TG 2, 60% of pigs in TG 3, 80% of pigs in TG 4, 20% of pigs in TG 5, 10% of pigs in TG 6, 20% of pigs in TG 7 and 0% of pigs in TG 8 possessed protective HI antibody levels. On Day 21, for the H3N2 strain of SIV, 20% of pigs in TG 3 possessed protective HI antibody levels. More importantly, in this experiment, Emulsigen®-DL90 once again produced the highest antibody levels followed by Emulsigen®-D, indicating the generation of the highest level of protective immunity of all adjuvants tested in this experiment. Generation of higher antibody titer levels enables using lower levels of antigen, helping to reduce vaccine costs.

It was expected that the water-in-oil-in-water adjuvants (WOW) would produce much higher antibody responses as this category of adjuvant is considered to be most effective with numerous antigens. Both WOW adjuvants produced extreme injection site reactivity as visually observed by the attending veterinarian (data not shown) which would normally suggest stimulation of a very high immune response.

The Carbigen™ adjuvant administered intranasally did not produce an IgG HI or ELISA response (data not shown). However, when IgA responses were measured using an ELISA specific for SIV IgA detection, this group (TG 8) was the only group that produced a response which remained high at 42 days (FIG. 7). Carbigen™ is an adjuvant that is known to have mucoadhesive properties. Therefore, it is more appropriate for use with intranasally administered antigens. In this case, an inactivated antigen, when administered intranasally with Carbigen™ adjuvant stimulated a high IgA response as measured in the serum of the pigs.

Conclusion

In both Example 6 and Example 7, Emulsigen®-DL90 produced the highest HI (IgG) antibody levels, indicating the generation of the highest level of protective immunity of all adjuvants tested in these experiments. Emulsigen®-D also produced very high antibody titers. These titers were two to four fold higher than the antibody titers produced by the adjuvant from a commercially available SIV vaccine adjuvant. Both these adjuvants produced higher titers than either a nanoparticle adjuvant or two WOW adjuvants evaluated in these Experiments. Additionally, it was shown that a mucoadhesive adjuvant (Carbigen™) produced a very high IgA response in serum when used to adjuvant the inactivated SIV antigen.

Example 8

SIV (IAV-S) Early Proteins as Inactivated Vaccines Administered Intranasally

In this example, antigens are prepared by extracting early proteins from SIV (IAV-S) produced in tissue culture. Such proteins are called early proteins because they are produced within the first 2-10 hours of tissue culture infection by subtypes of SIV (IAV-S). Such subtypes are typically H1N1 and H3N2 but can by any other of the subtypes of this virus. Early proteins are produced by infecting tissue culture cells grown in flasks, roller bottles or bioreactors with an SIV (IAV-S) virus subtype. Optionally, Trypsin can be used to enhance the infection with the viruses. The infected cells are then incubated for between 2 and 10 hours at 35-37° C. after which the supernatant is removed and the early proteins in the cells are released. The release of the early proteins is accomplished by freezing and then thawing the cells sheet in the presence of a buffer or by addition of a buffer such as one containing TRIS, EDTA and TRITON-X-100, NP40 or other equivalent surfactant.

The early proteins are then inactivated using any of the typical inactivating agents such as binary ethyleneimine, formalin, formaldehyde or betapropiolactone. If a TRIS, EDTA, surfactant extraction process is used, an additional inactivating agent may not be necessary as the virus is already inactivated.

These early proteins of SIV (IAV-S) are then formulated into a vaccine by adding mucoadhesive adjuvant(s). One of these adjuvants can be Carbigen™ It is expected that this inactivated SIV (IAV-S) vaccine can be administered intranasally to pigs to produce an IgA response that would be able to overcome the maternal antibody in such pigs. It is also expected that such proteins may be cross-protective, unlike the hemagglutin and neuraminidase proteins of SIV (IAV-S).

IV. Statements

Disclosed here are embodiments of a composition formulated for mucosal administration to an animal, the composition comprising inactivated bacterial antigens and at least one mucoadhesive adjuvant. The mucoadhesive adjuvant may be selected for intranasal administration, and/or may comprise a polymer, an oil-in-water emulsion, a saponin, a nanoparticle, a surfactant, a lipid, or a combination thereof. In some embodiments, the mucoadhesive adjuvant comprises a carbomer or nanoparticle, and may comprise polyacrylic acid.

In any of the above embodiments, the inactivated bacterial and/or viral antigens may be selected from antigens from *Streptococcus suis, Haemophilus parasuis, Actinobacillus suis* or a combination thereof, from swine influenza virus (SIV or IAV-S), porcine reproductive and respiratory syndrome virus (PRRSv), porcine epidemic diarrhea virus (PEDV), rotavirus, or a combination thereof, or any other types of bacteria or viruses wherein disease is introduced via a mucosal membrane. In certain embodiments, the inactivated bacterial antigens comprise antigens from at least one strain or serovar of *Streptococcus suis* and at least one strain or serovar of *Haemophilus parasuis*; antigens from at least one strain or serovar of *Haemophilus parasuis* and at least one strain or serovar of *Actinobacillus suis*; and/or antigens from at least one strain or serovar of *Streptococcus suis* and at least one strain or serovar of *Actinobacillus suis*. In particular embodiments, the inactivated bacterial antigens comprise antigens from at least one strain or serovar of *Streptococcus suis*, at least one strain or serovar of *Haemophilus parasuis* and at least one strain or serovar of *Actinobacillus suis.*

In some embodiments, the inactivated antigens are selected from whole culture bacteria, subunits that have been extracted or separated from the culture, extracts, antigens obtained from recombinant organisms other than *S. suis, A. suis* or *H. parasuis* but which protect against *S. suis, A. suis* or *H. parasuis* infection or challenge, inactivated vector-delivered antigens, inactivated recombinant organisms carrying *S. suis, A. suis, H. parasuis* antigens, or a combination thereof.

The composition may further comprise one or more additional antigens selected from antigens of *M. hyorhinis, M. hyosynoviae, P. multocida, B. bronchiseptica, E. rhusiopathiae, S. cholerasuis, S. typhimurium, C. perfringens, C. difficile, E. coli*, porcine rotaviruses, swine influenza virus, porcine reproductive and respiratory syndrome virus, porcine epidemic diarrhea virus, or porcine parvo virus.

The composition may further comprise an inactivating agent. In some embodiments, the inactivating agent is formaldehyde, formalin, binary ethyleneimine, thimerosal, beta propiolactone, or a combination thereof.

The composition may further comprise a diluent, preservative, antimicrobial agent, or a combination thereof.

In some embodiments, the inactivated antigens are present in an amount of from about $10^2$ to about $10^{10}$ CFU/mL.

The animal may be a pig. In some embodiments, the animal is a neonatal or nursery pig.

In some embodiments, the composition is a vaccine.

In particular embodiments, the composition comprises inactivated antigens of *Streptococcus suis, Haemophilus parasuis, Actinobacillus suis* or a combination thereof, and a mucoadhesive adjuvant comprising polyacrylic acid, and wherein the composition is formulated for intranasal administration.

Also disclosed herein is a method, comprising administering mucosally to an animal an effective amount of a first composition according to any one of the embodiments disclosed herein. The animal may be a pig, and in some embodiments, the pig is a neonatal pig or a nursery pig. The pig may be 10 days old or less, 5 days old or less, or 3 days old or less.

In some embodiments, administering mucosally comprises administrating intranasally.

Administering mucosally an effective amount of the first composition may comprise administering mucosally an amount of the first composition sufficient to produce an IgA immune response in the pig, compared to a pig that is not mucosally administered the first composition.

In some embodiments, the method further comprises administering a second composition comprising inactivated antigens of *Streptococcus suis, Haemophilus parasuis, Actinobacillus suis* or a combination thereof. The second composition may be administered intranasally or intramuscularly. In some embodiments, administering the second composition comprises administering the second composition within two to six weeks of the administration of the first composition.

Also disclosed herein are a method of vaccinating swine against diseases of *Streptococcus suis, Haemophilus parasuis, Actinobacillus suis* or a combination thereof, the method comprising administering inactivated one or more antigens from *Streptococcus suis, Haemophilus parasuis, Actinobacillus suis* or a combination thereof, to a pig by an intranasal route. And a method for reducing the incidence or lessening the severity of at least one clinical sign associated with *S. suis, A. suis* or *H. parasuis*, the method comprising administering mucosally to a pig the composition according to any one of the above statements.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11000585B2). An electronic copy of the "Sequence Listing" will also be available from the USPTO upon request and payment of the fee set forth in 37 CFR 1.19(b)(3).

We claim:

1. A aqueous solution formulated for mucosal administration to an animal, the aqueous solution comprising inactivated bacterial and/or viral antigens and a single adjuvant such that a concentration of adjuvant in the composition is from 5% to 70% w/w, wherein the single adjuvant is an aqueous polyacrylic acid-based mucoadhesive adjuvant.

2. The aqueous solution of claim 1, wherein the inactivated bacterial and/or viral antigens are selected from antigens from *Streptococcus suis, Haemophilus parasuis, Actinobacillus suis*, swine influenza virus, porcine respiratory and reproductive syndrome virus, porcine epidemic diarrhea virus, or a combination thereof.

3. The aqueous solution of claim 1, wherein the inactivated bacterial and/or viral antigens are selected from antigens from *Streptococcus suis, Haemophilus parasuis, Actinobacillus suis*, or a combination thereof.

4. A method, comprising administering to a swine mucosal membrane the aqueous solution of claim 1.

5. The method of claim 4, wherein the polyacrylic acid-based mucoadhesive adjuvant facilitates an IgA response in the swine.

6. The method of claim 4, wherein the aqueous solution is administered intranasally to the swine.

7. The method of claim 4, wherein the aqueous solution comprises inactivated bacterial antigens.

8. The method of claim 4, wherein the aqueous solution further comprises a surfactant.

9. A method of inducing an immune response in a swine, comprising administrating to the swine the aqueous solution of claim 1.

10. The method of claim 9, wherein inducing an immune response comprises inducing an IgA response in the swine.

11. The aqueous solution of claim 1, wherein the inactivated antigens are inactivated bacterial antigens.

12. The aqueous solution of claim 1, wherein the inactivated antigens are inactivated viral antigens.

13. The aqueous solution of claim 1, further comprising a surfactant.

14. The aqueous solution of claim 13, wherein the surfactant is a detergent.

15. The aqueous solution of claim 1, consisting essentially of the inactivated antigens, a surfactant, and the single adjuvant such that a concentration of adjuvant in the aqueous solution is from 5% to 70% w/w.

16. The aqueous solution of claim 1, further comprising culture media.

17. The aqueous solution of claim 1, further comprising an inactivating agent selected from formaldehyde, formalin, binary ethyleneimine, thimerosal, beta-propiolactone, or a combination thereof.

18. The aqueous solution of claim 1, comprising the inactivated antigens, a surfactant, and the mucoadhesive adjuvant such that a concentration of adjuvant in the composition is from 5% to 70% w/w, and wherein the aqueous solution is formulated for intranasal administration to swine.

19. A method, comprising mucosally administering to a swine an aqueous solution comprising:

an inactivated antigen;

culture media; and an aqueous polyacrylic acid-based mucoadhesive adjuvant;

wherein on administration the aqueous solution does not cause irritation to mucosa.

20. The method of claim 19, wherein a concentration of adjuvant in the aqueous solution is from 5% to 70% w/w.

21. The method of claim 19, wherein the aqueous solution comprises:

the inactivated antigen;

the culture media;

a surfactant;

an inactivating agent; and from 5% to 70% w/w of the adjuvant.

22. An aqueous suspension, comprising inactivated bacterial and/or viral antigens, cell fragments, and a single adjuvant such that a concentration of the single adjuvant in the aqueous suspension is from 5% to 70% w/w, wherein the single adjuvant is an aqueous polyacrylic acid-based mucoadhesive adjuvant.

23. The aqueous suspension of claim 22, wherein the inactivated bacterial and/or viral antigens are selected from antigens from *Streptococcus suis, Haemophilus parasuis, Actinobacillus suis*, swine influenza virus, porcine respiratory and reproductive syndrome virus, porcine epidemic diarrhea virus, or a combination thereof.

24. A method of inducing an immune response in a swine, comprising administrating to the swine the aqueous suspension of claim 22.

25. The method of claim 24, wherein the aqueous suspension is administered intranasally to the swine.

* * * * *